United States Patent [19]

Michl et al.

[11] 4,236,922
[45] Dec. 2, 1980

[54] DENTAL ALLOY OF BISMUTH-TIN WITH ADDITIONS OF AG, SB AND CU

[75] Inventors: Rudy Michl, Schaan; Peter Dorsch, Vaduz, both of Liechtenstein

[73] Assignee: Etablissement Dentaire Ivoclar, Schaan, Liechtenstein

[21] Appl. No.: 974,658

[22] Filed: Mar. 16, 1978

[30] Foreign Application Priority Data

Mar. 22, 1977 [DE] Fed. Rep. of Germany ....... 2712517

[51] Int. Cl.³ .............................................. C22C 33/00
[52] U.S. Cl. .............................. 75/134 D; 75/134 N; 75/175 H; 75/175 R
[58] Field of Search ............ 75/134 D, 175 A, 175 R, 75/134 N

[56] References Cited

U.S. PATENT DOCUMENTS

| | | | |
|---|---|---|---|
| 1,812,567 | 6/1931 | Strasser | 75/175 A |
| 3,079,455 | 2/1963 | Haba | 136/5 |
| 3,549,355 | 12/1970 | Postma | 75/134 |

FOREIGN PATENT DOCUMENTS 876602  5/1953  Fed. Rep. of Germany ........ 75/175 A

*Primary Examiner*—L. Dewayne Rutledge
*Assistant Examiner*—Upendra Roy
*Attorney, Agent, or Firm*—Sprung, Felfe, Horn, Lynch & Kramer

[57] ABSTRACT

A novel alloy comprising bismuth and tin which is characterized by the co-presence of silver and/or antimony. Particularly described is a dental alloy comprising:

1. 30 to 74 weight percent bismuth
2. 19 to 69.9 weight percent tin
3. Either
    A. Silver in an amount of 0.1 to 5 weight percent; or
    B. Antimony in an amount of 0.1 to 7 weight percent; or
    C. Silver and antimony in a combined amount of 0.1 to 7 weight percent, the proportion of silver being not more than about 5% by weight.

24 Claims, No Drawings

DENTAL ALLOY OF BISMUTH-TIN WITH ADDITIONS OF AG, SB AND CU

BACKGROUND OF THE INVENTION

1. Field of the invention

This invention relates to a bismuth/tin alloy. More especially this invention relates to a dental alloy comprising bismuth and tin as base elements and silver and/or antimony as adjuvant elements. This invention particularly contemplates a dental alloy comprising 30 to 74 weight percent bismuth, 19 to 69.9 weight percent tin and either:

A. Silver in an amount of 0.1 to 5 weight percent; or
B. Antimony in an amount of 0.1 to 7 weight percent; or
C. Silver and antimony in a combined amount of 0.1 to 7 weight percent, the proportion of silver being not more than about 5% by weight.

2. Discussion of Prior Art

The first step in the manufacture of dentures is for the dentist to take a case of the patient's jaw or an individual tooth, using suitable impression materials. The following are examples of suitable impression materials: elastomers, polysulfide elastomers (thiocols), silicones, hydrocolloids, alginates, plaster and the like.

The dental technician prepares a positive model from the negative mold of patient's jaw or tooth. For this purpose, he uses various model materials, which may expand or shrink. Since the impression materials are also subject to changes in volume, it is important to process the material so as to reduce the tolerance limit to a minimum. This reduces the possible combinations of impression materials and model materials.

The following model materials are available: plaster, plastics, cement, low-melting alloys, amalgams, electroplated metals and metal die-casting alloys. Out of these substances, plaster, plastics and cement are subject to relatively large changes in volume. In addition, plaster softens when heated over 100° C. and is unsuitable as a model material if the polymerization temperatures used are relatively high, e.g., in the manufacture of bridges. There is also a risk of damage through scratching, wear or fracture.

Low-melting casting alloys used as model materials contain, e.g., lead, tin, bismuth, and cadmium and melt at approximately 70° C. These materials are unsuitable in combination with any thermoplastic impression substances. They also have high surface tension, with the result that fine details cannot be very accurately reproduced. Finally, lead and cadmium are poisonous and therefore cannot be used as components of dental alloys.

Copper and silver amalgams are difficult to process when used as model materials, since they take 10 to 12 hours to harden and may release poisonous mercury vapors during processing. Consequently, they are not often used today.

Electroplated metals are applied by electroplating thermoplastic or elastomeric impression materials. The electroplated metal is usually copper, and the remaining cavities are backed up or lined with plastics or plaster. The dimensional accuracy of this method varies, since the casting impression swells and changes in the electroplating bath. The time taken to manufacture a model—6 to 24 hours—is also excessive.

It is also known to make models from metal die-casting alloys. These are conventional industrial bismuth-tin alloys melting at 138°–170° C., depending on their composition. The dimensional stability can be controlled via the bismuth content, since pure bismuth expands on solidifying. Difficulties occur, however, when spraying narrow spaces, e.g., with regard to surface quality when preparing lower front tooth stumps. In addition, the casting materials are not satisfactoryly wetted by metal in all cases. There are also problems regarding treatment with the lining material. The alloys are somewhat brittle, so that pieces of metal may split off during treatment.

It is an object of this invention, therefore, to improve the known bismuth/tin based die-casting alloys so that they are particularly suitable for use in dental technology. It is a further object to increase the hardness of such alloys without simultaneously making them brittle. Another object is to improve the surface, which is particularly desirable for dental use. A further object is to provide an alloy which is easily removed from the impression materials. When the alloys are sprayed on in layers, the individual layers must adhere firmly to one another and also the lining material.

SUMMARY OF THE INVENTION

Broadly, this invention comtemplates a bismuth/tin alloy containing silver and/or antimony. The alloy of this invention can also contain copper if required. Thus, this invention contemplates, in particular, a dental alloy comprising 30 to 74 weight percent bismuth and 19 to 69.9 weight percent tin and either:

A. Silver in an amount of 0.1 to 5 weight percent; or
B. Antimony in an amount of 0.1 to 7 weight percent; or
C. Silver and antimony in a combined amount of 0.1 to 7 weight percent, the proportion of silver being not more than about 5 percent by weight.

The dental alloy can also contain approximately 0.1 to 1 weight percent copper, in which case the total quantity of all admixtures must not exceed approximately 5 weight percent in case A or approximately 7 weight percent in cases B and C. Preferably, the quantity of admixtures B and C or the total quantity of all admixtures does not exceed approximately 5 weight percent.

It is surprising that the accuracy of detail when spraying the alloys on an impression material could be improved by the inclusion of silver and/or antimony in a known bismuth-tin alloy composition. Also provided is an increase in hardness without increasing the brittleness of the alloy. This is particularly valued by the dental technician, since the material is largely scratch-resistant during processing. No metal parts are observed to break loose from the alloys according to the invention. Visual and microscopic examination shows that the accuracy of reproduction is surprisingly high.

When the alloy according to the invention are sprayed, the individual layers are firmly bonded to one another and to the lining materials. Particular advantageous are synthetic resins and cast metal alloys as lining materials. Plaster can also be used as a lining material if the subsequent processing temperatures are below 100° C.

Preferably, the alloys according to the invention have a melting or solidification range between approximately 120° and 300° C. Since modern polymerization devices operate at temperatures above 90° C., preferably at 120° C., the alloys used must not have a lower melting point than the model materials. Even plaster cannot be used as a model material at the aforementioned temperatures.

It is not desirable to exceed the aforementioned melting range during the metal-spraying process, since technological difficulties in the spray gun occur at temperatures above 300° C.

Antimony alone, if added, improves the surface and gives the required scratch resistance to the model. The amount of antimony can be up to approximately 7 weight percent without excessively increasing the melting point of the alloy.

Silver, if added alone, appreciably improves the surface, which becomes completely shiny and smooth. At the same time, however, the melting point of the alloy is increased, so that it is not advisable to add more than 5 weight percent silver.

Antimony and silver, when added together, advantageously combined good surface properties and favorable melting ranges.

Copper improves the rheological properties of the alloy when sprayed.

Preferably the dental alloys according to the invention contain admixtures in approximately the following proportions:
(a) approximately 0.1 to 2.5 weight percent antimony or
(b) approximately 0.1 to 2.0 weight percent silver or
(c) approximately 0.2 to 4.5 weight percent antimony and silver together.

If copper is also used, the total amount thereof is preferably approximately 0.2 to 0.8 weight percent.

A particularly preferred dental alloy is characterized in that it contains the following admixtures:
(a) 1.0 to 2.5 weight percent antimony or
(b) 0.5 to 1.0 weight percent silver or
(c) approximately 2.0 to 3.0 weight percent antimony and silver and, if required, also contains:
(d) 0.5 weight percent copper.

Advantageously, the dental alloy according to the invention contains approximately 36 to 70 weight percent, preferably approximately 36 to 65 weight percent bismuth and approximately 63.9 to 25 weight percent, preferably approximately 63.9 to 30 weight percent, tin.

Other preferred ranges for the main constituents are as follows: approximately 52 to 59 weight percent bismuth and approximately 47 to 36 weight percent tin; approximately 38 to 45 weight percent bismuth and 61 to 50 weight percent tin; and approximately 47 to 53 weight percent bismuth and 52 and 42 weight percent tin.

Die-casting alloys based on bismuth-tin eutectic are particularly suitable. Such alloys are characterized by substantially the following composition:

| | | | |
|---|---|---|---|
| 56.5 ± 1.5 | weight percent bismuth; | 41 ± 1.5 | weight percent tin |
| 1.5 ± 1 | weight percent antimony and/or | 1.5 ± 1 | weight percent silver |
| 0.5 ± 0.5 | weight percent copper | | |

The melting point, surface and hardness of these alloys are good and appreciably superior to conventional alloys having the corresponding main constituents. Examples of these alloys are given in the Table, Nos. 14 to 26.

Particularly suitable alloys having low expansion during solidification are characterized by the following composition:

| | | | |
|---|---|---|---|
| 39 ± 1.5 | weight percent bismuth | 58 ± 1.5 | weight percent tin |
| 1.5 ± 1 | weight percent antimony and/or | 1.5 ± 1 | weight percent silver |
| 1.5 ± 0.5 | weight percent copper | | |

These alloys are shown in the Table, Nos. 28 to 40.

It has also been found possible to use alloys which, owing to their relatively high bismuth content, expand somewhat more during solidification. This effect, however, is cancelled out if the casting material shrinks, which it often inevitably does.

The last-mentioned alloys are characterized by substantially the following compositions:

| | | | |
|---|---|---|---|
| 68 ± 2 | weight percent bismuth | 28.5 ± 1.5 | weight percent tin |
| 1.5 ± 1 | weight percent antimony and/or | 1.5 ± 1 | weight percent silver |
| 0.5 ± 0.5 | weight percent copper | | |

Examples of these alloys are given in the Table, Nos. 2 to 12.

Use can be made also of alloys having the following composition:

| | | | |
|---|---|---|---|
| 48.5 ± 1.5 | weight percent bismuth | 48.5 ± 1.5 | weight percent tin |
| 2.5 ± 1 | weight percent antimony and/or | 0.5 ± 0.4 | weight percent silver |

TABLE

| Alloy | Bismuth | Tin | Antimony | Silver | Copper | Vickers hardness 0.2 kg (kg/mm²) | Solidification range Liquid °C. | Solidification range Solid °C. | Surface, accuracy of reproduction |
|---|---|---|---|---|---|---|---|---|---|
| 1* | 70 | 30 | | | | 21.5 | 182 | 134 | Dull, porous, blurred |
| 2 | 66.5 | 28.5 | 5 | | | 28.8 | 231 | 137 | Shining, smooth, sharp |
| 3 | 68.3 | 29.2 | 2.5 | | | 26.2 | 197 | 141 | " |
| 4 | 69.3 | 29.7 | 1 | | | 24.6 | 185 | 140 | " |
| 5 | 66.5 | 28.5 | | 5 | | 25.6 | 290 | 133 | " |
| 6 | 68.3 | 29.2 | | 2.5 | | 24.2 | 225 | 135 | " |
| 7 | 69.3 | 29.7 | | 1 | | 23.1 | 190 | 135 | " |
| 8 | 66.5 | 28.5 | 2.5 | 2.5 | | 28.1 | 230 | 134 | " |
| 9 | 68.6 | 29.4 | 1.0 | 1.0 | | 25.2 | 195 | 135 | " |
| 10 | 66.5 | 28.5 | 3 | 1.5 | 0.5 | 27.1 | 240 | 131 | " |
| 11 | 67.9 | 29.1 | 2.5 | | 0.5 | 26.0 | 241 | 140 | " |
| 12 | 67.9 | 29.1 | | 2.5 | 0.5 | 24.9 | 239 | 132 | " |
| 13* | 58 | 42 | | | | 22.0 | 138 | 138 | Dull, slightly porous, smudgy |
| 14 | 55 | 40 | 5 | | | 34.4 | 254 | 140 | Shining, smooth, sharp |

TABLE-continued

| Alloy | Bismuth | Tin | Antimony | Silver | Copper | Vickers hardness 0.2 kg (kg/mm²) | Solidification range Liquid °C. | Solidification range Solid °C. | Surface, accuracy of reproduction |
|---|---|---|---|---|---|---|---|---|---|
| 15 | 56.6 | 40.9 | 2.5 | | | 29.2 | 188 | 138 | " |
| 16 | 57.4 | 41.6 | 1 | | | 24.0 | 141 | 135 | " |
| 17 | 55 | 40 | | 5 | | 27 | 295 | 131 | " |
| 18 | 56.6 | 40.9 | | 2.5 | | 26.2 | 234 | 131 | " |
| 19 | 57.4 | 41.6 | | 1 | | 25.5 | 195 | 129 | " |
| 20 | 55 | 40 | 2.5 | 1.5 | | 33.1 | 231 | 138 | " |
| 21 | 56 | 40.5 | 2.5 | 1.0 | | 31.2 | 190 | 138 | " |
| 22 | 56.3 | 40.7 | 2.5 | 0.5 | | 29.1 | 182 | 136 | " |
| 23 | 56.8 | 41.2 | 1.0 | 1.0 | | 25.4 | 188 | 133 | " |
| 24 | 55 | 40 | 2.5 | 2.0 | 0.5 | 32.2 | 235 | 135 | " |
| 25 | 56.3 | 40.7 | 2.5 | | 0.5 | 30.3 | 233 | 139 | " |
| 26 | 56.3 | 40.7 | | 2.5 | 0.5 | 28.2 | 233 | 139 | " |
| 27* | 40 | 60 | | | | 23.9 | 177 | 139 | Dull, porous, blurred |
| 28 | 38 | 57 | 5 | | | 31.2 | 231 | 137 | Shining, smooth, sharp |
| 29 | 39 | 58.5 | 2.5 | | | 29.0 | 180 | 140 | " |
| 30 | 39.6 | 59.4 | 1 | | | 27.8 | 179 | 137 | " |
| 31 | 38 | 57 | | 5 | | 31.5 | 294 | 133 | " |
| 32 | 39 | 58.5 | | 2.5 | | 31.0 | 233 | 133 | " |
| 33 | 39.6 | 59.4 | | 1 | | 26.8 | 159 | 129 | " |
| 34 | 38 | 57 | 2.5 | 2.5 | | 30.8 | 239 | 141 | " |
| 35 | 38.6 | 57.9 | 2.5 | 1.0 | | 29.9 | 174 | 137 | " |
| 36 | 38.8 | 58.2 | 2.5 | 0.5 | | 29.4 | 158 | 138 | " |
| 37 | 39.2 | 58.8 | 1.0 | 1.0 | | 28.0 | 191 | 139 | " |
| 38 | 38.4 | 57.6 | 2.5 | 1.0 | 0.5 | 30.5 | 249 | 138 | " |
| 39 | 38.8 | 58.2 | 2.5 | | 0.5 | 29.6 | 245 | 139 | |
| 40 | 38.8 | 58.2 | | 2.5 | 0.5 | 28.9 | 245 | 135 | " |

*Alloys 1, 13 and 27 are not according to the invention

The following example illustrates the use of the alloys according to the invention.

EXAMPLE

The dentist prepares an alginate impression of a patient's lower jaw. The dental technician sprays the impression with an alloy according to the invention, until a relatively thin but resistant layer has deposited on the impression. The thickness of the metal layer is usually approximately 0.5 to 2 mm. If, for example, the alloy is No. 36 in the Table, the spray gun used has a metal container which is electrically heated to approximately 180° to 190° C., controlled by a thermostat, up to the spray nozzle.

The back of the metal is rough, suitable for backing up with a highly liquid cold-setting synthetic resin. After about 20 minutes the synthetic resin has hardened and the entire substance is released from the alginate impression, thus obtaining a metal-coated model (or positive working model) reinforced with synthetic resin, showing very high accuracy of reproduction. It is substantially insensitive to damage during subsequent treatment.

The dental technician then processes the model in the appropriate manner, e.g., by inserting teeth or preparing crowns or entire bridges. The resulting dental work (e.g., a bridge) on the metal-coated model, can have its appropriate surfaces covered with a plastic facing. In order to harden the plastic facing, the metal-coated model, bridge and plastic facing are all placed in a polymerization device. The plastic is usually polymerized under pressure at 120° C.

After polymerization, the vessel is opened and the polymerized dental component can easily be released from the metal surface. It is then further processed by the dental technician in conventional manner.

The invention is not restricted to the application given, since the alloys according to the invention can also be used for other applications in dental technology.

We claim:

1. A dental alloy consisting essentially of 30 to 74 weight percent bismuth, 19 to 69.9 percent weight and either:
A. Silver in the amount of 0.1 to 5 weight percent;
B. Silver and antimony in the combined amount of 0.1 to 7 weight percent, the proportion of silver being not more than about 5% by weight said alloy containing up to 1 weight 1 percent copper.

2. A dental alloy according to claim 1 containing approximately 0.1 to 1 weight percent copper, the total amount of all of said elements silver, antimony and copper being not more than about 5% by weight when said alloy contains only silver as adjuvant element and not more than approximately 7% by weight if said alloy contains antimony inadmixture with silver.

3. A dental alloy according to claim 1 containing antimony in admixture with silver, the combined amount of antimony and silver being not more than about 5% by weight.

4. A dental alloy according to claim 2 containing:
A. Silver in the amount of 0.1 to 2.0 weight percent, or
B. Silver and antimony in the combined amount of 0.2 to 4.5 weight percent.

5. A dental alloy according to claim 4 containing 0.2 to 0.8 weight percent copper.

6. A dental alloy according to claim 4 containing:
A. Silver in the amount of 1 weight percent, or
B. Silver and antimony in the combined amount of 2.0 to 3.0 weight percent.

7. A dental alloy according to claim 6 containing approximately 0.5 weight percent copper.

8. A dental alloy according to claim 1 containing approximately 36 to 70 percent bismuth and approximately 25 to 63.9 weight percent tin.

9. A dental alloy according to claim 8 containing 36 to 65 weight percent bismuth and 30 and 63.9 weight percent tin.

10. A dental alloy according to claim 9 containing 52 to 59 weight percent bismuth and 36 to 47 percent by weight tin.

11. A dental alloy according to claim 9 containing 38 to 45 weight percent bismuth and 50 to 61 weight percent tin.

12. A dental alloy according to claim 9 containing 47 to 53 weight percent bismuth and 42 to 52 weight percent tin.

13. A dental alloy according to claim 1 having a melting point between 120° and 300° C.

14. A dental alloy according to claim 1 having the composition:

| | |
|---|---|
| 56.5 ± 1.5 weight percent bismuth; | 41 ± 1.5 weight percent tin; 1.5 ± 1 weight percent silver; |
| 0.5 ± 0.5 weight percent copper. | |

15. A dental alloy according to claim 1 having the following composition:

| | |
|---|---|
| 39 ± 1.5 weight percent bismuth; | 58 ± 1.5 weight percent tin; 1.5 ± 1 weight percent silver; |
| 0.5 ± 0.5 weight percent copper. | |

16. A dental alloy according to claim 1 having the following composition:

| | |
|---|---|
| 68 ± 2 weight percent bismuth; | 28.5 ± 1.5 weight percent tin; 1.5 ± 1 weight percent silver; |
| 0.5 ± 0.5 weight percent copper. | |

17. A dental alloy according to claim 1 having the following composition:

| | |
|---|---|
| 48.5 ± 1.5 weight percent bismuth; | 48.5 ± 1.5 weight percent tin; 0.5 ± 0.4 weight percent silver. |

18. A dental alloy according to claim 1 containing a mixture of silver and antimony.

19. A dental alloy according to claim 4 containing a mixture of antimony and silver.

20. A dental alloy according to claim 6 containing a mixture of silver and antimony.

21. A dental alloy according to claim 14 containing a mixture of silver and antimony.

22. A dental alloy according to claim 15 containing a mixture of silver and antimony.

23. A dental alloy according to claim 16 containing a mixture of silver and antimony.

24. A dental alloy according to claim 17 containing a mixture of silver and antimony.

* * * * *

UNITED STATES PATENT AND TRADEMARK OFFICE
CERTIFICATE OF CORRECTION

PATENT NO. : 4,236,922
DATED : December 2, 1980
INVENTOR(S) : Rudy Michl; Peter Dorsch It is certified that error appears in the above-identified patent and that said Letters Patent are hereby corrected as shown below:

| Column | Line | |
|--------|------|---|
| 6 | 42 | delete "1" 2nd occurrence |

Signed and Sealed this

Fourteenth Day of April 1981

[SEAL]

Attest:

RENE D. TEGTMEYER

Attesting Officer     Acting Commissioner of Patents and Trademarks